US010363384B2

(12) United States Patent
Dyche et al.

(10) Patent No.: US 10,363,384 B2

(45) Date of Patent: Jul. 30, 2019

(54) SYSTEM AND METHOD OF REMOTELY MONITORING AND/OR MANAGING THE TREATMENT OF A PLURALITY OF SUBJECTS WITH AEROSOLIZED MEDICAMENT

(75) Inventors: Anthony Dyche, Hayling Island (GB); Ian Philip Rabbetts, Hayling Island (GB); Jonathan Stanley Harold Denyer, Chichester (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 99 days.

(21) Appl. No.: 14/003,245

(22) PCT Filed: Mar. 16, 2012

(86) PCT No.: PCT/IB2012/051261

§ 371 (c)(1), (2), (4) Date: Sep. 5, 2013

(87) PCT Pub. No.: WO2012/123919

PCT Pub. Date: Sep. 20, 2012

(65) Prior Publication Data

US 2014/0000599 A1 Jan. 2, 2014

Related U.S. Application Data

(60) Provisional application No. 61/453,248, filed on Mar. 16, 2011.

(51) Int. Cl.

| | |
|---|---|
| ***A61M 16/00*** | (2006.01) |
| ***A61M 16/14*** | (2006.01) |
| ***G16H 20/13*** | (2018.01) |

(52) U.S. Cl.

CPC ...... *A61M 16/0051* (2013.01); *A61M 16/021* (2017.08); *A61M 16/14* (2013.01); *G16H 20/13* (2018.01)

(58) Field of Classification Search

CPC ............... A61M 16/0051; A61M 16/14; G06F 19/3462; G06F 19/3456; G06F 19/3418; G01F 19/00

(Continued)

(56) References Cited

U.S. PATENT DOCUMENTS

| | | | | |
|---|---|---|---|---|
| 5,524,645 A | | 6/1996 | Wills | |
| 6,529,446 B1 | * | 3/2003 | de la Huerga ........ | A61J 7/0084 368/10 |

(Continued)

FOREIGN PATENT DOCUMENTS

| | | |
|---|---|---|
| EP | 1068875 A2 | 1/2001 |
| EP | 1738786 A1 | 1/2007 |

(Continued)

OTHER PUBLICATIONS

E. T. Zemanick et al; "Measuring and Improving Respiratory Outcomes in Cystic Fibrosis Lung Disease: Opportunities and Challenges to Therapy", Journal of Cystic Fibrosis, Elsevier, NL, vol. 9, No. 1, Jan. 1, 2010, pp. 1-16, XP026834327.

(Continued)

*Primary Examiner* — Gregory A Anderson
*Assistant Examiner* — Margaret M Luarca
(74) *Attorney, Agent, or Firm* — Michael W. Haas

(57) ABSTRACT

Therapy regimes of a plurality of subjects are remotely monitored and/or managed, wherein the therapy regimes include reception of aerosolized medicament. This enables users such as medical care providers, researchers, clinic administrators, and/or other users to monitor and/or manage the therapy regimes of the plurality of subjects through a centralized access point. This reduces physical requirements of proximity for the users and/or the subjects, alleviates the administrative burden placed on the users to manage and/or (Continued)

monitor individual therapy regimes, and/or provides other enhancements over convention systems.

25 Claims, 10 Drawing Sheets

(58) Field of Classification Search
USPC .................................................... 128/203.14
See application file for complete search history.

(56) References Cited

U.S. PATENT DOCUMENTS

| | | | | |
|---|---|---|---|---|
| 6,670,885 | B2 | 12/2003 | Kosaka | |
| 6,863,224 | B2 | 3/2005 | Terada et al. | |
| 6,958,691 | B1 * | 10/2005 | Anderson ............ | A61B 5/0002 128/200.14 |
| 7,451,760 | B2 | 11/2008 | Denyer | |
| 2001/0022279 | A1 * | 9/2001 | Denyer ............ | A61M 15/0045 206/438 |
| 2002/0065685 | A1 * | 5/2002 | Sasaki ................ | A61M 15/025 705/3 |
| 2003/0036683 | A1 * | 2/2003 | Kehr ..................... | G06F 19/325 600/300 |
| 2003/0200964 | A1 * | 10/2003 | Blakley ............ | A61M 15/0065 128/200.23 |
| 2004/0107961 | A1 * | 6/2004 | Trueba ............. | A61M 15/0085 128/200.16 |
| 2004/0153338 | A1 * | 8/2004 | Kim ...................... | G06F 19/322 705/2 |
| 2006/0047368 | A1 | 3/2006 | Maharajh | |
| 2007/0000490 | A1 | 1/2007 | De Vries et al. | |
| 2007/0061165 | A1 * | 3/2007 | Ash ....................... | G06F 19/322 705/2 |
| 2007/0282177 | A1 * | 12/2007 | Pilz ........................ | A61B 5/411 600/301 |
| 2008/0004540 | A1 | 1/2008 | Nakao | |
| 2009/0030382 | A1 | 1/2009 | Brandt | |
| 2009/0138814 | A1 * | 5/2009 | Schneider ........... | G06F 19/3406 715/780 |
| 2009/0149800 | A1 | 6/2009 | Durand | |
| 2009/0151718 | A1 | 6/2009 | Hunter | |
| 2009/0194104 | A1 * | 8/2009 | Van Sickle ........... | A61M 15/00 128/203.12 |
| 2009/0294521 | A1 * | 12/2009 | de la Huerga .......... | A61J 1/035 235/375 |
| 2010/0121654 | A1 | 5/2010 | Portnoy et al. | |
| 2010/0161353 | A1 * | 6/2010 | Mayaud ................ | G06F 19/322 705/3 |

FOREIGN PATENT DOCUMENTS

| | | | |
|---|---|---|---|
| JP | 2001357132 | A | 12/2001 |
| JP | 2003159332 | A | 6/2003 |
| JP | 2008108121 | A | 5/2008 |
| WO | 200051491 | | 9/2000 |
| WO | 2004071368 | A2 | 8/2004 |
| WO | 2011021117 | A1 | 2/2011 |
| WO | 2011021118 | A1 | 2/2011 |

OTHER PUBLICATIONS

Evan Whitby et al; "Development of a Low-Pressure Aerosol Sampler", Rev. Sci. Instrum. vol. 60, No. 7, Jul. 1995K pp. 3955-3965.
Denyer, "The I-NEB Adaptive Aerosol Delivery (AAD) System", Medica Mundi, vol. 54, No. 3, 2010, pp. 54-58.
Denyer et al, "Adaptive Aerolsol Delivery (AAD) Technology", Expert Opinion Drig Delivery, vol. 1, No. 1, 2004, pp. 165-176.
Okumura et al, "3D Roadmapping in Neuroendovascular Procedures—An Evaluation", Medica Mundi, vol. 54, No. 3, 2010, pp. 5.
Carrafiello et al, "Percutaneous Transthoracic Needle Biopsy of Pulmonary Nodules Under Xperguide Cone-Beam CT Guidance", Medica Mundi, 2010, vol. 54, No. 3, pp. 12-17.
Schrofel et al, "Transcatheter Aortic Valve Implantation in a Hybrid Operating Room Using Heart Navigator", Medica Mundi, vol. 54, No. 3, 2010, pp. 18-25.
Smits et al, "Visualization of Stent Malapposition in the Mid Left Anterior Descending Artery Using Stent Boost", Medica Mundi, 2010, vol. 54, No. 3, pp. 26-27.
Intermezzo, "Intellispace Portal: Access to Data and Processing From Any Location", Medica Mundi, 2010, vol. 54, No. 3, p. 59.
Kobeiter et al, "Translumbar Type II Endoleak Empolization Using Real-Time Needle Guidance and Fluoroscopy Overlay on Pre-Treatment CTA", Medica Mundi, 2010, vol. 54, No. 3, pp. 32-34.
Fischbach et al, "MR-Guided Ablative Therapy of Malignant Liver Tumors Employing the Panorama HFO Open MR Scanner", Medica Mundi, 2010, vol. 54, No. 3, p. 35-40.
Perioperative Management of Obstructive Sleep Apnea Patients, Medica Mundi, 2010, vol. 54, No. 3, pp. 41-46.
Nikander et al, "The Early Evolution of Nebulizers", Medica Mundi, 2010, vol. 54, No. 3, pp. 47-53.
McNamara, P.S. et al., "Open Adherence Monitoring Using Routine Data Download from an Adaptive Aerosol Delivery Nebuliser in Children with Cystic Fibrosis", Journal of Cystic Fibrosis, vol. 8, Issue 4, Jul. 2009, pp. 258-263.

* cited by examiner

500

600

| Drug name (601) | I-neb chamber latch colour (602) | I-neb chamber volume (ml) (603) | Number of chamber fills per treatment (A) (604) | Clinician prescription (B) (605) | Number daily treatments = A x B (606) | Daily horn on time @ delivery rate (0.5 ml/min) (607) |
|---|---|---|---|---|---|---|
| Promixin | Grey | 0.3 | 1 | 0 | 0 | |
| Promixin 28 day off/on | Grey | 0.3 | 1 | 0 | 0 | |
| Tobramycin 28 day on/off | Purple | 0.5 | 2 | 0 | 0 | |
| Aztreonam 28 day on/off | Purple | 0.5 | 2 | 0 | 0 | |
| Dornase Alpha | Grey | 0.3 | 1 | 0 | 0 | |
| Salbutamol | Grey | 0.3 | 1 | 0 | 0 | |
| Hypertonic Saline | Purple | 0.5 | 1 | 0 | 0 | |
| | | | | | TNT = $\sum$ [] (total number of treatments) (608) | Mean horn on time = $\sum$ times/TNT (609) |

| Drug name | I-neb chamber latch colour | I-neb chamber volume (ml) | Number of chamber fills per treatment (A) | Clinician prescription (B) | Number daily treatments = A x B | Daily horn on time @ delivery rate (0.5 ml/min) |
|---|---|---|---|---|---|---|
| Promixin 28 day off/on | Grey | 0.3 | 1 | 2 | 0 | |
| Tobramycin 28 day on/off | Purple | 0.5 | 2 | 2 | 4 | = 0.5 x 4 x 60/0.5 [240 sec] |
| | | | | | TNT = $\sum$ [4] (total number of treatments) | Mean horn on time = $\sum$ times/TNT [60 sec] |

FIG. 7

SYSTEM AND METHOD OF REMOTELY MONITORING AND/OR MANAGING THE TREATMENT OF A PLURALITY OF SUBJECTS WITH AEROSOLIZED MEDICAMENT

The invention relates to remotely monitoring and/or managing the therapy of a plurality of subjects, wherein the therapy comprises the delivery of aerosolized medicament.

Aerosol drug delivery devices are often used in medical treatment to provide drugs in a form that can be inhaled by a patient. Medicaments in powder, liquid, or other forms may be aerosolized using various techniques (e.g., using a piezoelectric member) to enable the medicament to be absorbed through the patient's air passage. As such, aerosol medicament treatments may be administered for respiratory ailments (e.g., asthma) or other treatments where a patient inspires drugs while breathing.

Aerosol medicament treatments are typically designed to administer a specific daily dosage of medicament(s) over a given period of time. However, some aerosolized medicaments, such as antibiotics, may be prescribed to be delivered intermittently to the subject following a particular on/off cycle. This is done to reduce the likelihood that the bacteria being treated forms a resistance to the antibiotic which might happen if it is delivered indefinitely. The on/off cycle includes a delivery period during which the aerosolized medicaments are delivered to the subject and a non-delivery period during which the aerosolized medicaments are not delivered to the subject. Existing systems and techniques for administering aerosolized medicaments that follow an on/off cycle require an operator to change the prescription at the end of the delivery period and at the end of the non-delivery period of the on/off cycle so that the specific daily dosage of medicaments to be delivered to the subject for the next period can be determined.

One aspect of the invention relates to a system configured to remotely monitor the therapy of at least one subject, wherein the therapy includes the delivery of a plurality of aerosolized medicaments and wherein at least one of the plurality of aerosolized medicaments is delivered following an on/off cycle of a predetermined duration, said on/off cycle including a delivery period during which said at least one aerosolized medicament is delivered to said subject and a non-delivery period during which said at least one aerosolized medicament is not delivered to said subject, the system comprising: a server comprising one or more processors configured to execute computer program modules, the computer program modules comprising: an information acquisition module configured to obtain, over a communications network, therapy information for said subject, wherein therapy information for said subject includes information related to a respiratory capacity of said subject and information conveying one or more breathing parameters of the respiration of said subject during the delivery of the aerosolized medicaments; a user interface module configured to generate a definition of a user interface that enables a user to selectively view said therapy information and to enter prescription data relating to said plurality of medicaments; and a treatment calculation module configured to calculate a total number of daily treatments to be delivered to said subject based on said prescription data, wherein said calculation module is configured to automatically change the total number of daily treatments for said plurality of aerosolized medicaments when the therapy enters the delivery period and/or the non-delivery period of the on/off cycle of said at least one aerosolized medicament.

Another aspect of the invention relates to a computer implemented method of remotely monitoring the therapy of at least one subject, wherein the therapy includes the delivery of a plurality of aerosolized medicaments and wherein at least one of the plurality of aerosolized medicaments is delivered following an on/off cycle of a predetermined duration, said on/off cycle including a delivery period during which said at least one aerosolized medicament is delivered to said subject and a non-delivery period during which said at least one aerosolized medicament is not delivered to said subject, and wherein the method is implemented by a server comprising one or more processors configured to execute one or more computer program modules, the method comprising: executing one or more computer program modules on the one or more processors of the server to obtain, over a communications network, therapy information for said subject, wherein therapy information for said subject includes information related to a respiratory capacity of the subject and information conveying one or more breathing parameters of the respiration of said subject during the delivery of the aerosolized medicaments; executing one or more computer program modules on the one or more processors of the server to generate a definition of a user interface that enables a user to selectively view said therapy information and to enter prescription data relating to said plurality of medicaments; and executing one or more computer program modules on the one or more processors of the server to calculate a total number of daily treatments to be delivered to said subject based on said prescription data, wherein said total number of daily treatments is automatically changed for said plurality of aerosolized medicaments when the therapy enters the delivery period and/or the non-delivery period of the on/off cycle of said at least one aerosolized medicament.

Another aspect of the invention relates to a system configured to remotely monitor the therapy of at least one subject, wherein the therapy includes the delivery of a plurality of aerosolized medicaments and wherein at least one of the plurality of aerosolized medicaments is delivered following an on/off cycle of a predetermined duration, said on/off cycle including a delivery period during which said at least one aerosolized medicament is delivered to said subject and a non-delivery period during which said at least one aerosolized medicament is not delivered to said subject, the system comprising: means for obtaining, over a communications network, therapy information for said subject, wherein therapy information for said subject includes information related to a respiratory capacity of said subject and information conveying one or more breathing parameters of the respiration of said subject during the delivery of the aerosolized medicaments; means for generating a definition of a user interface that enables a user to selectively view said therapy information and to enter prescription data relating to said plurality of medicaments; and means for calculating a total number of daily treatments to be delivered to said subject based on said prescription data, wherein the total number of daily treatments for said plurality of aerosolized medicaments is automatically changed by calculating means when the therapy enters the delivery period and/or the non-delivery period of the on/off cycle of said at least one aerosolized medicament.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

FIG. 6 schematically illustrates a table that shows patient prescription data on server, according to one or more embodiments of the invention.

FIG. 7 schematically illustrates a table that shows patient prescription data on server, according to one or more embodiments of the invention.

Figure 8:
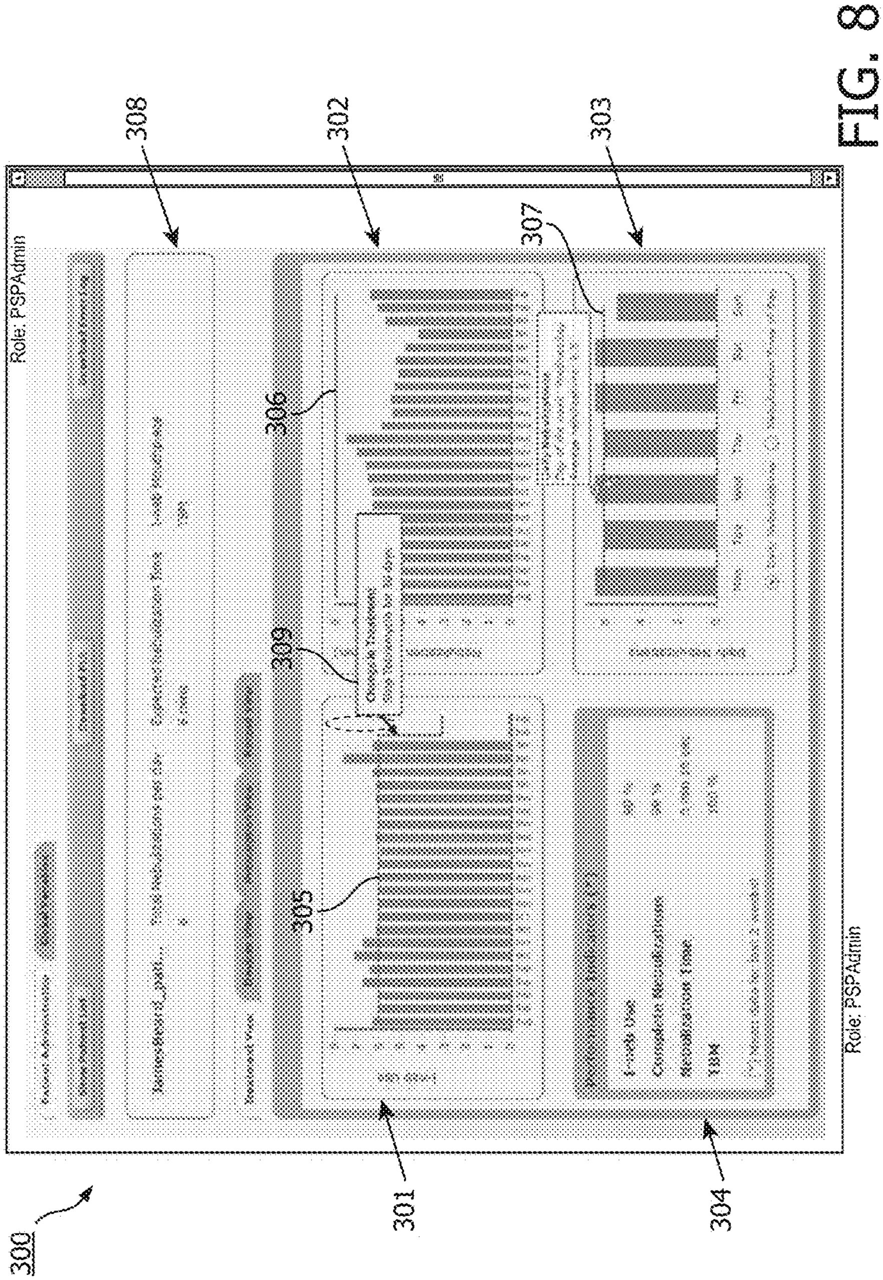

FIG. 8 illustrates a graphical user interface displayed on a display of a client computer platform, according to one or more embodiments of the invention.

Figure 9:
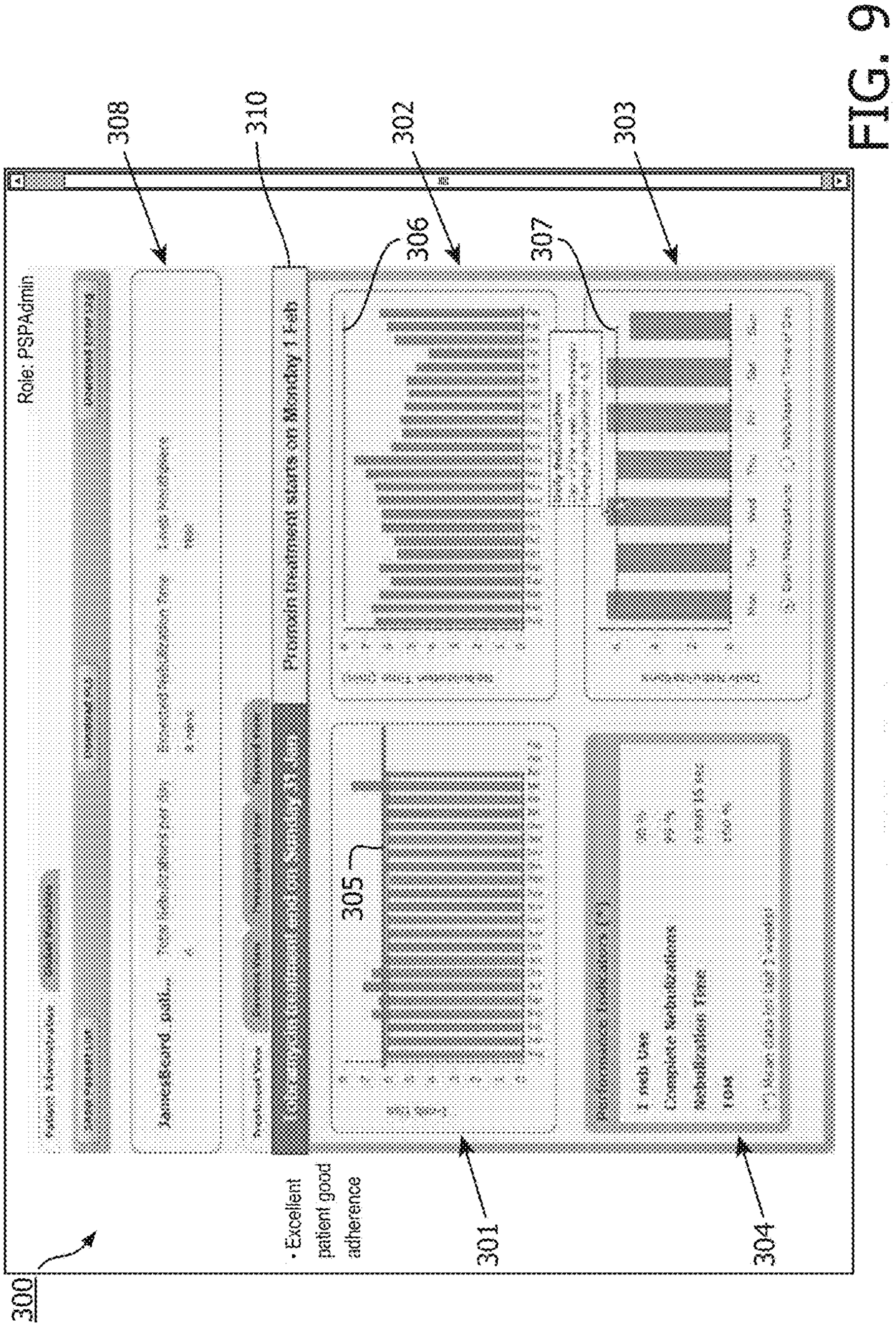

FIG. 9 illustrates a graphical user interface displayed on a display of a client computer platform, according to one or more embodiments of the invention.

Figure 10:
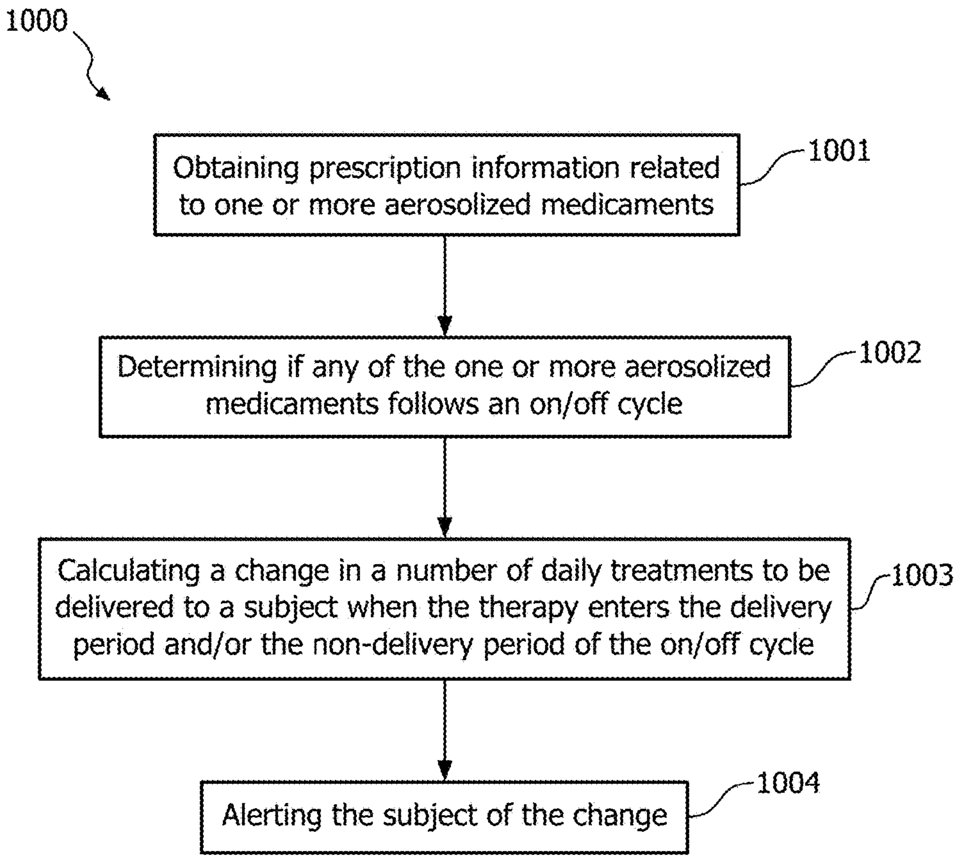

FIG. 10 illustrates a flow-chart of a method of remotely monitoring and/or managing therapy regimes of one or more subjects, in accordance with one or more embodiments of the invention.

Figure 1:
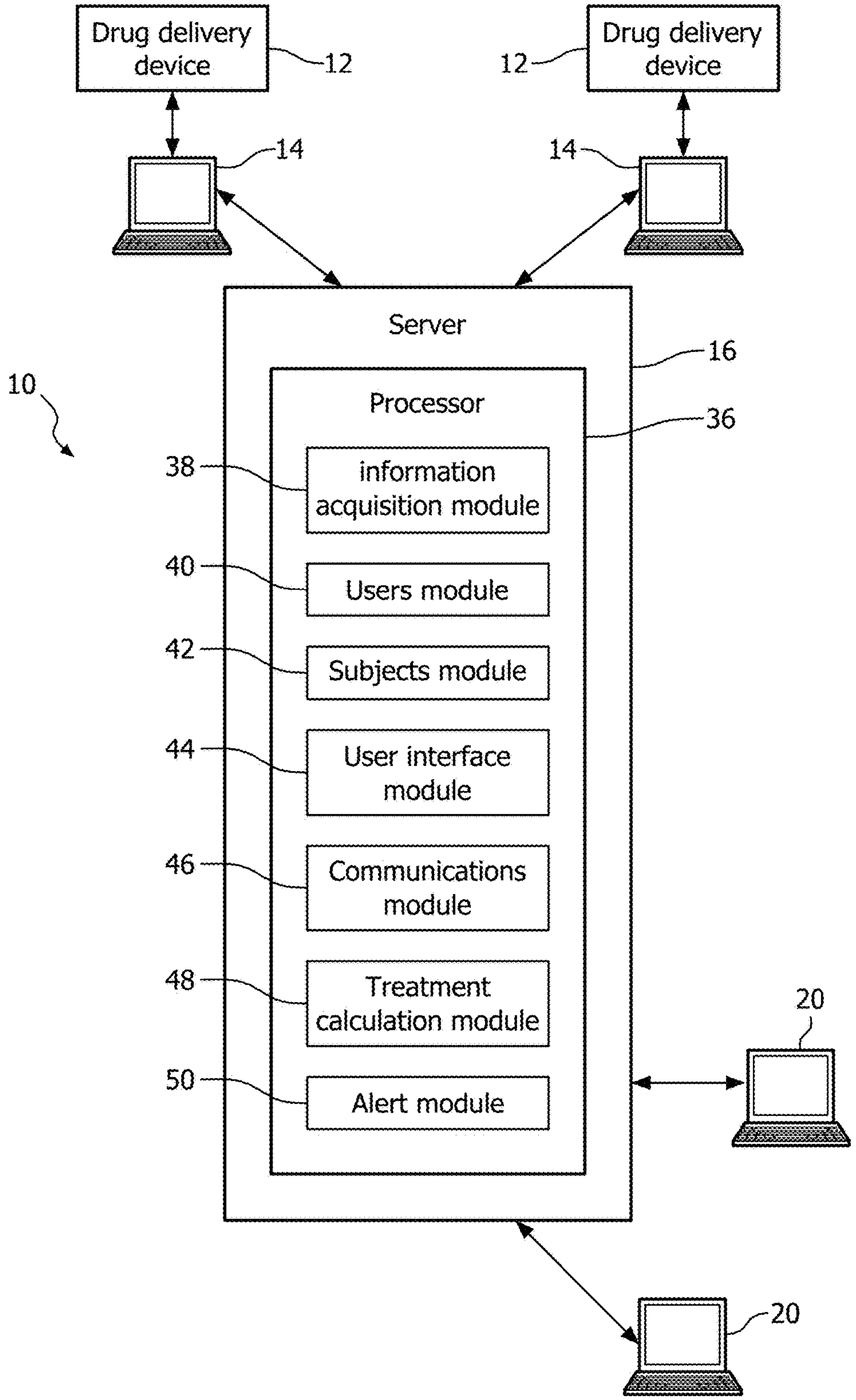
FIG. 1 illustrates a system configured to remotely monitor and/or manage therapy regimes of a plurality of subjects, according to one or more embodiments of the invention.

FIG. 1 illustrates a system 10 configured to remotely monitor and/or manage therapy regimes of a plurality of subjects, wherein the therapy regimes include reception of aerosolized medicament. System 10 enables users such as medical care providers, researchers, clinic administrators, and/or other users to monitor and/or manage the therapy regimes of the plurality of subjects through a centralized access point. This reduces physical requirements of proximity for the users and/or the subjects, alleviates the administrative burden placed on the users to manage and/or monitor individual therapy regimes, and/or provides other enhancements over convention systems. In one embodiment, system 10 includes a plurality of drug delivery devices 12, a plurality of client computing platforms 14 associated with the plurality of subjects, a server 16, one or more client computing platforms 20 associated with one or more users of system 10, and/or other components.

The drug delivery devices 12 are configured to deliver aerosolized medicament to the subjects. For example, drug delivery devices 12 may include one or more of a nebulizer, a metered dose inhaler, a metered dose inhaler spacer, a dry powder inhaler, and/or other devices capable of delivering aerosolized medicament. One or more of drug delivery devices 12 may be configured for use in a clinical setting, in a home setting, or both. Typically, a given one of drug delivery devices 12 is considered to be associated with a specific subject, and therapy information originating from the given one of drug delivery devices 12 is assumed to be relevant to the subject associated therewith. However, this should not be viewed as limiting.

Figure 2:
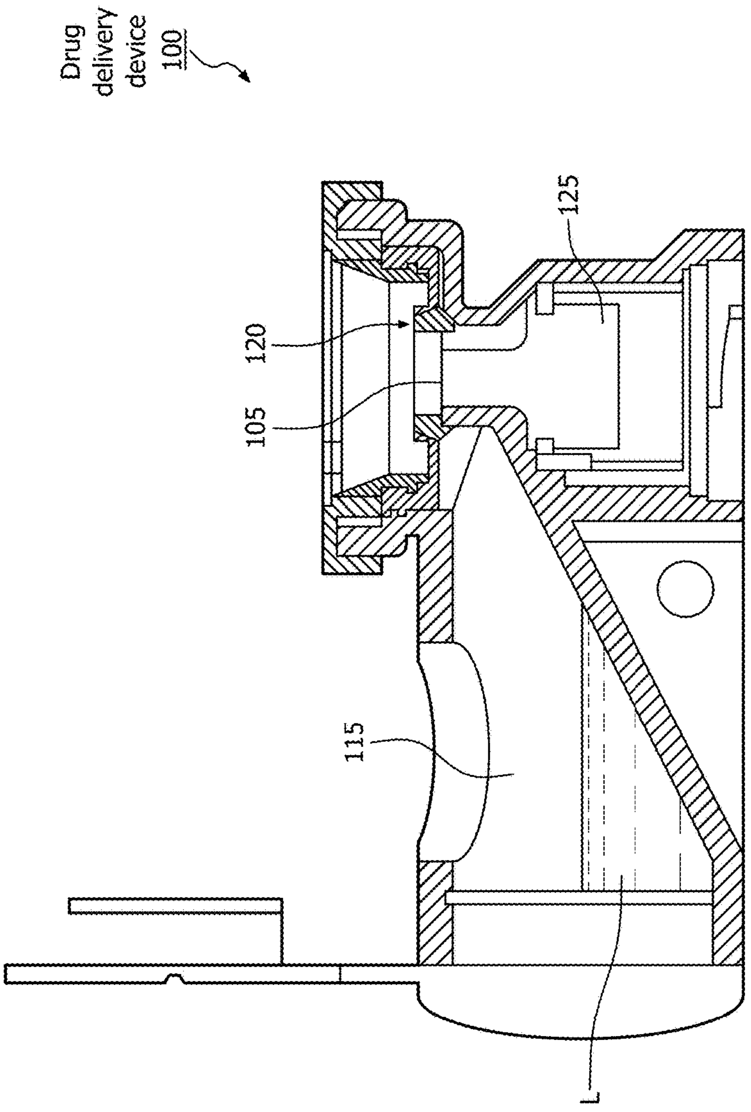
FIG. 2 illustrates an exemplary aerosol drug delivery device, in accordance with one or more embodiments of the invention.

Referring to FIG. 2, this figure illustrates one embodiment of an aerosol drug delivery device 100 that is used to administer an aerosol form of a liquid medicament L for inspiration by a subject. For example, device 100 may include a reservoir 115 for containing a liquid medicament L and an aerosol generator 120.

The aerosol generator 120, in one embodiment, may take the form of a mesh member 105 in combination with a horn oscillating member 125 for nebulizing or otherwise aerosolizing the liquid drug L. However, as discussed in more detail later, this type of aerosol generator 120 is a non-limiting example of the many different types of aerosol generators that can be used within the scope of the present invention. The mesh member 105, in one embodiment, may be mounted to an end surface of a distal end of the horn oscillating member 125. The drug delivery device 100 may incorporate any suitable power source (as will be discussed later) to electrically drive the horn oscillating member 125. As such, the horn oscillating member 125 may force the liquid L through a plurality of fine apertures or pores in mesh member 105, thereby producing an aerosolized form of liquid medicament L that can be inspired by a subject.

The reservoir 115 can be any chamber, container, or canister that may contain a dosage of liquid medicament. In various implementations, aerosol generator 120 and reservoir 115 device 100 may be constructed and arranged as described in U.S. Pat. No. 6,863,224 ("the '224 patent"), issued Mar. 8, 2005, entitled "Liquid Spray Device," the disclosure of which is hereby incorporated by reference in its entirety. It should be emphasized, however, that the '224 patent discloses but one example of the type of aerosol generator and reservoir that can be employed with the teachings of the present invention, as will be apparent from the farther descriptions herein.

As noted above, aerosol generator 120 may produce the aerosolized form of the liquid medicament L using any type of nebulizer or aerosol generating mechanism that can turn the liquid medicament L into aerosol and/or droplets that can be inhaled by the subject. For example, as illustrated in FIG. 2, liquid medicament L disposed in reservoir 115 may reach a proximal point of contact between a distal end of oscillating horn member 125 and mesh 105 (e.g., a metallic or non-metallic screen having a plurality of fine apertures). A power source may deliver a pulse of power to aerosol generator 120, causing the horn 125 to vibrate and drive the liquid medicament through the mesh 105, detaching the liquid into an aerosolized form. It will be apparent, however, that various other aerosol generators 120 may be used, including jet nebulizers, vibrating meshes, vibrating horns, nozzles that use Raleigh breakup theory, piezoelectric crystal technology, or other nebulizing devices or techniques known in the art. It should be appreciated that these are non-limiting examples of the type of aerosol generators that can be used with the present invention, and that any suitable device that can nebulize or aerosolize a liquid drug for this application can be used.

As can be appreciated from the discussion above, aerosol generator 120 may be configured to receive pulses of power from the power source until all of the liquid in the chamber 115 has been aerosolized for inspiration by the subject. As such, a uniform drug dosage may be administered in every treatment instance. For various reasons, however, aerosol generator 120, in itself may not necessarily maintain a uniform duration of treatment for every treatment. For example, a breathing pattern of a patient (e.g., an inhalation to exhalation ratio, a breathing frequency, etc.) may impact a rate of drug administration, potentially impacting treatment time. In another example, the mesh 105 of aerosol generator 120 may become dirty over a course of treatment, or a reusable mesh may become dirtier over a course of successive treatments, or meshes may be interchanged between treatments, or the mesh may degrade over time, all of which may be among contributing factors potentially impacting treatment time (e.g., by reducing a rate at which generator 120 outputs the aerosolized drug).

Referring back to FIG. 1, the client computing platforms 14 may include one or more of a laptop computer, a desktop computer, a netbook, a smartphone, and/or other client computing platforms.

Each client computing platform 14 is, at least intermittently, communicatively coupled with a corresponding one of drug delivery devices 12 to obtain information therefrom and/or provide instructions or other communications thereto. This communication may be accomplished, for example, via a wireless connection (e.g., Bluetooth, WiFi, infrared, WiMax, and/or other wireless connection), and/or wired connection (e.g., USB, FireWire, etc.). These communications may include relatively short data uploads (e.g., "synching") that are instigated by determinations by a client computing platform 14 that the corresponding drug delivery device 12 is currently linked (e.g., via wireless media), and are executed in the background on client computing platforms 14 (without substantial disruption to other processes and/or applications being executed thereon). In one embodiment, communications between client computing platform 14 and drug delivery device 12 include more dedicated sessions in which processes executed on the client computing platform 14 related to the communication with client computing platform 14 are given a higher priority, and/or at least a portion of a display associated with the client computing platform 14 provides a graphical user interface associated with the use and/or functionality of drug delivery device 12 in real-time or near real-time.

Client computing platform 14 may include one or more processors configured to execute one or more computer programming modules. At least some of the one or more computer programming modules executed on the one or more processors of client computing platform 14 include software modules associated with a software application that provides, for example the functionality to receive therapy information from drug delivery device 12 and to transmit the therapy information to server 16. These software modules are stored on electronic storage media that is accessible to the one or more processors of client computing platform 14. In one embodiment, no therapy information is stored on client computing platforms 14 and no therapy information is processed by client computing platforms 14. Rather, therapy information to be processed is transmitted to server 16.

The information received on client computing platform 14 from drug delivery device 12 may include, for instance, therapy information, which is transmitted to server 16. As will be discussed further below, the therapy information may include, for example, one or more of a total aerosol (e.g., a horn) actuation time, a total amount of time the patient spent inhaling, a total amount of time the patient spent exhaling, information related to the power level at which drug delivery device 12 was operated during therapy, and/or other therapy information. Based on this information, client computing platform 14 may provide a user interface to the subject (and/or caregiver or other user) that enables the subject to access indications of the effectiveness of the therapy, the compliance of the patient with a prescribed therapy regime, the operational efficiency of drug delivery device 12, and/or other information related to the therapy.

As was stated above, client computing platforms 14 are communicatively linked with server 16. Communications between client computing platforms 14 and server 16 may be implemented via a network. This network may include, for example, the Internet and/or an intranet associated with a clinic (or set of clinics), a hospital (or set of hospitals), a research institution, and/or other entities.

Server 16 includes one or more computing platforms configured to serve information to a plurality of client applications being executed on client computing platforms. By way of non-limiting example, server 16 may include a Web server. In one embodiment, server 16 is a dedicated server platform that is solely executing computer modules associated with hosting and serving content. In one embodiment, server 16 is implemented on a computing platform that is performing other types of processing concomitant with the server functionality discussed herein. In this embodiment server 16 may be embodied in a computing platform such as a personal desktop or laptop computer that is configured to perform server functionality. Although server 16 is illustrated in FIG. 1 as an actually physically separate component, in one embodiment, server 16 is a virtual server accessible to client computing platforms 14 and 20 over the communications network(s).

As can be seen in FIG. 1, server 16 includes a processor 36. Processor 36 is configured to provide information processing capabilities in server 16. As such, processor 36 may include one or more of a digital processor, an analog processor, a digital circuit designed to process information, an analog circuit designed to process information, a state machine, and/or other mechanisms for electronically processing information. Although processor 36 is shown in FIG. 1 as a single entity, this is for illustrative purposes only. In some implementations, processor 36 may include a plurality of processing units. These processing units may be physically located within the same device, or processor 36 may represent processing functionality of a plurality of devices (e.g., a plurality of servers) operating in coordination to provide the functionality attributed herein to server 16.

Processor 36 is configured to execute one or more computer program modules. The one or more computer program modules may include one or more of an information acquisition module 38, a users module 40, a subjects module 42, a user interface module 44, a communications module 46, a treatment calculation module 48, an alert module 50 and/or other modules. Processor 36 may be configured to execute modules 38, 40 42, 46, 48, and/or 50 by software; hardware; firmware; some combination of software, hardware, and/or firmware; and/or other mechanisms for configuring processing capabilities on processor 36.

It should be appreciated that although modules 38, 40 42, 44, 46, 48, and/or 50 are illustrated in FIG. 1 as being co-located within a single processing unit, in implementations in which processor 36 includes multiple processing units, one or more of modules 38, 40 42, 44, 46, 48, and/or 50 may be located remotely from the other modules. The description of the functionality provided by the different modules 38, 40 42, 44, 46 48, and/or 50 set forth below is for illustrative purposes, and is not intended to be limiting, as any of modules 38, 40 42, 44, 46, 48, and/or 50 may provide more or less functionality than is described. For example, one or more of modules 38, 40 42, 44, 46, 48, and/or 50 may be eliminated, and some or all of its functionality may be provided by other ones of modules 38, 40 42, 44, 46, 48, and/or 50. As another example, processor 36 may be configured to execute one or more additional modules that may perform some or all of the functionality attributed below to one of modules 38, 40 42, 44, 46, 48, and/or 50.

The information acquisition module 38 is configured to obtain therapy information from a plurality of drug delivery devices, including drug delivery devices 12. In one embodiment, this includes communicating with client computing platforms 14 to receive therapy information that has been transferred from drug delivery devices 12 to client computing platforms 14, respectively. The therapy information obtained by information acquisition module 38 from client computing platforms 14 is received by information acquisition module 38 over the communications network linking server 16 with client computing platform 14. The transfer of therapy information from client computing platform 14 to information acquisition module 38 over the communications network may be initiated automatically (e.g., after additional therapy information has been obtained by client computing platform 14 from drug delivery device 12, at predetermined intervals, etc.), or manually by the subject via a command input to client computing platform 14.

The users module 40 is configured to manage one or more user profiles of users that are provided with access to therapy information obtained by server 16 from drug delivery devices 12. As used herein the term "user" may include a caregiver, a researcher, an administrator, and/or other individuals that should be provided with access to therapy information associated with a plurality of the subjects using drug delivery devices 12. The user profiles may include one or more of identification information (e.g., user ID, etc.) that enables the users to be identified and/or associated with particular user profiles, authentication information (e.g., login, password, etc.) that enables the users to be authenticated to server 16, configuration preferences associated with the users, and/or other information associated with the individual users.

It will be appreciated that the two drug delivery device 12 are not the only drug delivery devices for which server 16 receives therapy information. For example, in FIG. 1, additional drug delivery devices (not shown) are also communicatively linked with server 16 (e.g., via corresponding client computing platforms). In one embodiment, the information related to individual users included in the user profiles managed by users module 40 includes access privileges that indicate which drug delivery devices the individual users should be given access to. The access privileges may even indicate specific types of therapy information for which access should be given to a given user (e.g., information related to performance efficiency or effectiveness of a device, but not information related to patient respiratory capacity, treatment, and/or compliance).

The subjects module 42 is configured to manage a plurality of subject profiles that correspond to the subjects for which therapy information is obtained by information acquisition module 38. The subject profile corresponding to a given subject includes one or more of identification information identifying the subject (e.g., name, patient or subject number, etc.) and the therapy information obtained for the given subject. The subject profile corresponding to the given subject may include information related to which users should receive access to therapy information associated with the given subject.

In one embodiment, subjects module may be constructed and arranged as described in U.S. Patent Application Ser. No. 61/234,264, entitled "System and Method of Remotely Monitoring and/or Managing the Treatment of a Plurality of Subjects with Aerosolized Medicament," the disclosure of which is hereby incorporated by reference in its entirety.

The user interface module 44 is configured to generate a definition of a user interface for a user that enables the user to selectively view therapy information obtained by information acquisition module 38, information related to calculations determined by treatment calculation module 48, information generated by alert module 50, and/or other information. This includes enabling a user to select a specific subject or set of subjects, and to view information associated with the specific subject or set of subjects based on the selection. The user interface defined by the definition generated by user interface module 44 further enables a user to select an information type, analysis based on the therapy information, a specific view of selected information and/or analysis; and to view the selected information type and/or analysis in the selected view.

In one embodiment, the definition of the user interface generated by user interface module 44 includes a definition of a web page that can be viewed in a Web browser on a client computing platform. The definition of the web page may include, for example, HTML, dHTML, XML, JAVA, Flash, and/or information encoded in other formats that are readable by a Web browser. In one embodiment, the definition of the user interface generated by user interface module 48 is generated for a more specialized client side application. For example, the client side application may already include views for selectively viewing therapy information, and the definition of the user interface generated by user interface module 48 may include merely values for the therapy information that is viewable within a given view provided by the client side application. In this embodiment, the client side application receives the values for the therapy information included in the definition of the user interface that inserts some or all of the values (as appropriate) into the corresponding portions of a view.

User interface module 44, in one embodiment, generates a definition of a user interface that provides one or more views to the user that enable one or more parameters of the treatment regime prescribed for a patient or group of patients to be adjusted by the user. Adjustments entered through the user interface defined by the definition generated by user interface module 44 are then provided to the appropriate drug delivery device (e.g., drug delivery device 12) via server 16.

The communications module 46 is configured to provide the definition of the user interface generated by user interface module 44 to the user. In one embodiment, communications module 46 accomplishes this by serving the user interface to client computing platform 20 associated with the user. The client computing platform 20 may include one or more of a laptop computer, a desktop computer, a netbook, a smartphone, and/or other client computing platforms. The communications module 46 may serve the user interface to client computing platform 20 over a network. This network may include the Internet and/or an intranet associated with a clinic (or set of clinics), a hospital (or set of hospitals), or other entities. In order to view the defined user interface, client computing platform 20 may implement a versatile client application, like a web browser, to render the user interface based on the communication from communications module 20. As was mentioned above, in one embodiment, rather than a versatile client application like a web browser, client computing platform 20 may execute a client application that is specifically designed for viewing the user interface defined by communications module 46.

In one embodiment, the user interface defined by user interface module 44 enables the user to input communication directed toward a subject or group of subjects. This communication is then distributed by communications module 48 to the subject or group of subjects. The communication may be distributed to the subject or group of subjects via their drug delivery devices (e.g., via drug delivery device 12 by way of client computing platform 14), via one or more client computing devices associated with the subject or group of subjects, and/or via other communication devices associated with the subject or group of subjects (e.g., via SMS message, via voicemail, via automated phone call, etc.). These communications may include messages selected by the user from a predefined set of communications indicating action that the patient or group of patients should with respect to their drug delivery device(s), adjustments that should be made to the treatment regime prescribed for the patient or group of patients, adjustments that should be made by the patient or group of patients to respiration during treatment, and/or other messages. The user interface may present a set of communications to the user for transmission to the subject(s) based on analysis of therapy information obtained by information acquisition module 38.

In one embodiment, communications module 46 further enables subjects to transmit communications back to the user. For example, communications module 46 may be configured to receive communications input by a subject to drug delivery device 12 and/or client computing platform 14, and to provide such communication to the appropriate user (e.g., via client computing platform 14). These communications may be in response to communications received from the user (e.g., confirming a change and/or action indicated in a communication from the user has been made and/or taken), or may be instigated entirely by the subject.

It will be appreciated that enabling communication between server 16 and devices (e.g., drug delivery devices 12 and/or client computing platforms 14) associated with individual subjects provides various enhancements over previous systems. For example, the communication of therapy information associated with the different patients to a centralized entity (the server 16) provides users with centralized, convenient access to information needed to monitor and/or manage a plurality of disparate patients and/or drug delivery devices. Similarly, enabling a user to generate customized communication from the centralized entity to the individual patients facilitates a superior treatment experience for the patients.

In one embodiment, the users that are able to access therapy information via server 16 includes the actual patients receiving the therapy, not just caregivers, researchers, etc. In this embodiment, rather than executing a "thick" client application on client computing platform 14 and/or client computing platform 20 to monitor therapy, the patients may access therapy information from server 16 using a "thin" client application (like a web browser). This may reduce the costs associated with setting up and/or maintaining the system illustrated in FIG. 1 because it would remove costs associated with distributing, installing, maintaining, and updating specialized software on client computing platforms associated with the patients (e.g., client computing platform 14 and/or client computing platform 20).

Figure 3:
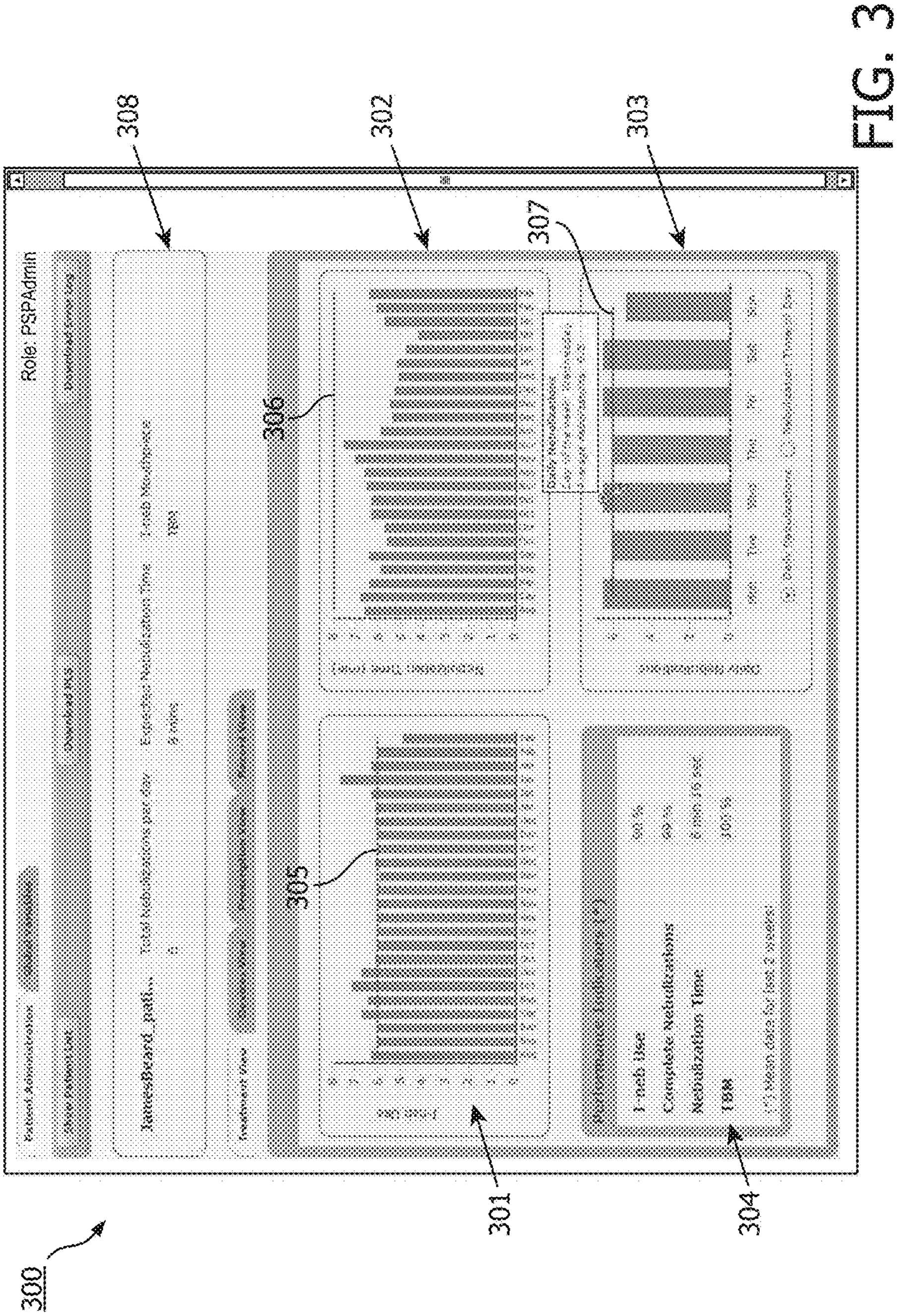
FIG. 3 illustrates a graphical user interface displayed on a display of a client computer platform, according to one or more embodiments of the invention.

Referring to FIG. 3, this figure shows a view 300 of the user interface defined by user interface module 44 that includes therapy information related to subject compliance to a treatment regime. This view 300 may be referred to as a "treatment view." As can be seen in FIG. 3, the treatment view 300 provides the user with information about the frequency and/or duration of treatments received by a subject or group of subjects, and/or other information.

In FIG. 3, the treatment view 300 includes a first graph 301 showing, for each week, the actual total number of daily nebulizations, a second graph 302 showing, for each week, the actual total daily nebulization time, and a third graph 303 showing, for a given week, the actual number of daily nebulizations. Although not shown in FIG. 3, third graph 303 can display, for a given week, the nebulization time for each day. As shown in FIG. 3, the treatment view further displays the expected or targeted total number of daily nebulizations, represented by line 305 in graph 301 and line 307 in graph 303, and the expected or targeted total daily nebulization time, represented by line 306 in graph 304. The expected total number of daily nebulizations and the expected daily nebulization time are also displayed in an area 308 at the top of treatment view 300. Treatment view 300 also displays a performance indicators summary 304 for the last two weeks of the therapy. However, this should not be viewed as limiting. In one embodiment, the summary may be averaged over a different number of weeks.

Figure 4:
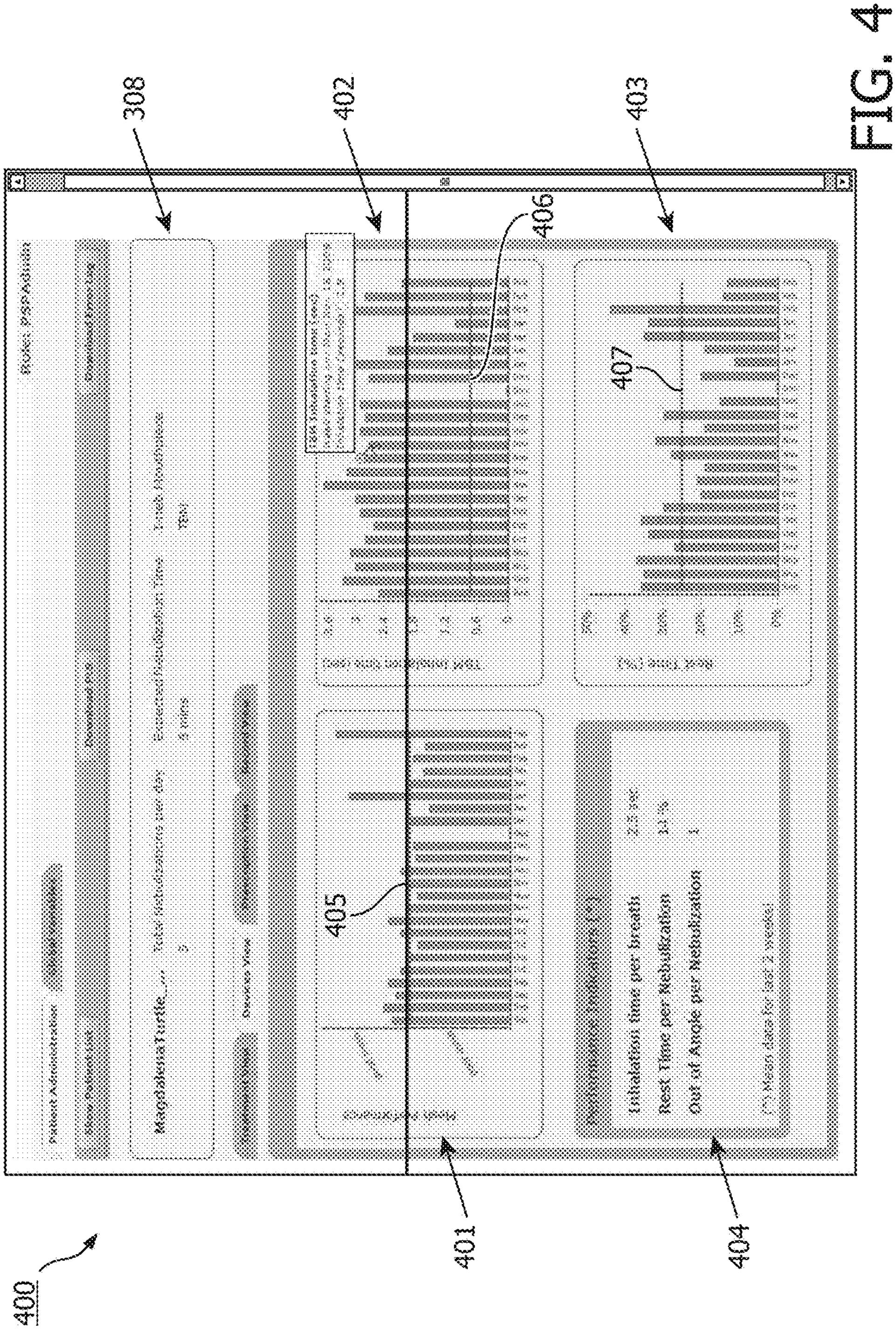
FIG. 4 illustrates a graphical user interface displayed on a display of a client computer platform, according to one or more embodiments of the invention.

Similarly, FIG. 4 illustrates an embodiment of the user interface defined by user interface module 44 in which the user interface includes a view 400 that presents therapy information to the user related to the performance of a drug delivery device used by a patient or group of patients. This view 400 may be referred to as a "device view." The device view 400 includes information related to metrics that quantify drug delivery device performance.

In FIG. 4, the metrics that are monitored include, for each week, the mesh performance of the drug delivery device shown in graph 401, the tidal breathing mode (TBM) inhalation time shown in graph 402 and the rest time shown in graph 403. Device view 400 further displays the targeted mesh performance, represented by line 405, the targeted TBM inhalation time represented by line 406 and the targeted rest time, represented by line 407. Likewise, a performance indicators summary 404 is also represented for the last two weeks of the therapy. However, this should not be viewed as limiting. In one embodiment, the summary may be averaged over a different number of weeks.

Other views that may be included in the user interface may include one or more of a prescription view, a record view, a subject grouping view, a respiratory capacity view, and/or other views. The prescription view includes information related to the therapy regime that has been prescribed for a subject or group of subjects. The record view includes information related to historical device usage and/or respiratory function of a subject or group of subjects. The subject grouping view enables the user to view, create, and/or manipulate groupings of subjects. The subject groupings may be established based on one or more of demographic information (e.g., age, ethnicity, sex, geographic location, education, socioeconomic classification, and/or other demographic information), medical condition, medicament received, therapy regime prescribed, respiratory capacity, and/or other information. This grouping may be done manually by the user and/or automatically by server 16.

Figure 5:
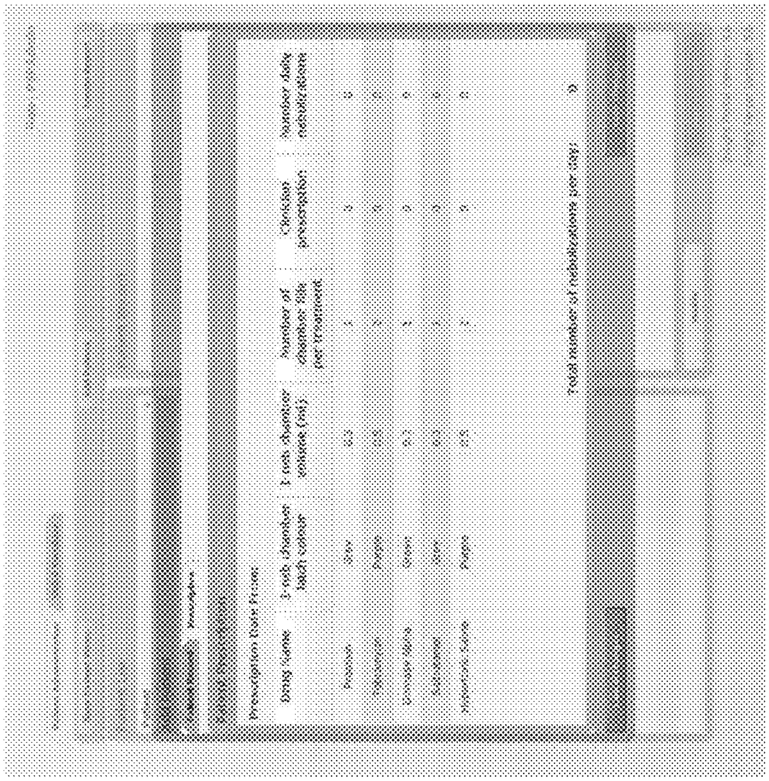
FIG. 5 illustrates a graphical user interface displayed on a display of a client computer platform, according to one or more embodiments of the invention.

For example, referring to FIG. 5, this figure shows one embodiment of a prescription view 500. For a given subject, the prescription view includes information related to the therapy regime that has been prescribed for the subject. This includes the name of each prescribed medicament, the clinician prescription (i.e. number of daily treatments for each medicament given in a range from 1 to 10) and the number of daily nebulizations. For each medicament volume to be delivered to the subject, the chamber volume of drug delivery device 12 and the number of chamber fills per treatment are displayed as pre set limits. These limits are determined from the medicament dose required (mg) to deliver the required therapeutic effects from the clinical trials conducted to approve each medicament. In one embodiment, prescription information for each patient shown in prescription view 500 is entered by the user (who can be a system administrator) into a prescription data form using user interface module 44.

FIG. 6 schematically illustrates one embodiment of the patient prescription data that are available on and/or processed by server 16. For illustrative purposes, patient prescription data have been arranged in a table 600. It will be appreciated that table 600 is not a graphical user interface. Rather, table 600 schematically illustrates the prescription information entered by the user and the various data that are processed by treatment calculation module 48 (e.g. number of daily treatments and/or the daily treatment time) of server 16. Note that columns 601-607 of table 600 are displayed in prescription view 500 of FIG. 5. Table 600 includes a first column 601 that contains the name(s) of the medicament(s) to be delivered during the therapy. For each medicament, the user interface module 44 enables the user to further identify whether the medicament should be cycled on/off, and the duration of the cycle (i.e. the delivery period of the cycle during which the medicament will be delivered to the subject and the non-delivery period during which the medicament is not delivered to the subject). This is desirable for some medicaments (e.g. antibiotics) in order to reduce the likelihood that the bacteria being treated forms a resistance to the antibiotic which might happen if it is delivered indefinitely. In the event a particular medicament should be cycled on/off, user interface module 44 is adapted to generate a definition of a user interface in which an extra row is automatically added in prescription view (this is schematically illustrated in table 600). Then, the user identifies whether the medicament is in the delivery period (on period) or the non-delivery period (off period) of the on/off cycle at the beginning of the treatment. In one embodiment, the beginning of the treatment starts on a Monday and the therapies start on the next Monday following a change in prescription.

In one embodiment, when a particular medicament should be delivered to the subject following an on/off cycle, system 10 is configured to enable the user to select one or more alternative medicaments to be delivered to the subject during the non-delivery period (off period) of that particular medicament. In one implementation, this is done using user interface module 44, which generates a definition of a user interface that prompts the user to determine if one or more alternative medicaments should be delivered during the non-delivery period of a particular medicament and, if so, the name(s) of, and prescription information for, the alternative medicament(s).

For example, in FIG. 6, table 600 lists 6 medicaments, 3 of which have a 28 days on/off cycle (Promixin, Tobramycin and Aztreonam). In FIG. 6, and for that particular week of treatment, Promixin is in the non-delivery period ("off/on" indicator in column 601), while both Tobramycin and Aztreonam are in the delivery period ("on/off" indicator in column 601). Conversely, and because the cycles for Promixin, Tobramycin and Aztreonam are the same, Promixin will be delivered during the non-delivery period of Tobramycin and Aztreonam.

In FIG. 6, the on/off cycle for the first entered medicament (Promixin) has a delivery period and a non-delivery period of equal duration. The delivery period is 4 weeks, or 28 days. During that period, Promixin will be delivered on a daily basis to the subject for 28 days. Then, after the first 28 day period, Promixin treatment will enter the non-delivery period, which also lasts 4 weeks, or 28 days. After that period, Promixin will enter a new active delivery period again. While the delivery periods of the medicaments shown in table 600 are set to 28 days, this is not limiting. It will be appreciated that the on/off cycle is determined based on the medicament and the clinician prescription. As a result, it will be appreciated that the on/off cycle may be of any duration and the duration of the delivery period may be different from the non-delivery period.

Table 600 further includes, for each medicament, a second column 602 that identifies the color code of the medicament, a third column 603 that identifies the chamber volume of the drug delivery device 12 that should be filled for the medicament, a fourth column 604 that identifies the number of chambers of the drug delivery device that should be filled per treatment, and a fifth column 605 that identifies, in a range from 1 to 10, the daily clinician prescription for the medicament. Data in columns 603 and 604 are displayed as preset limits in prescription view 500. As mentioned previously, these data are determined from the medicament dose required (mg) to deliver the required therapeutic effects from the clinical trials conducted to approve each medicament.

Referring back to FIG. 1, in one embodiment, treatment calculation module 48 is configured to calculate the number of daily treatments and the daily treatment time for each week of therapy based on information provided in table 600. The therapy may include the delivery of one or more aerosolized medicaments and/or the delivery of one or more aerosolized medicaments that follow(s) an on/off cycle of a predetermined duration. Calculations are performed at the beginning of the therapy and/or each time a new medicament is prescribed to the subject. As will be explained in more detail below, treatment calculation module 48 is further configured to automatically change the total number of daily treatments and/or the daily treatment time for the prescribed medicaments when the therapy enters or is about to enter the delivery period and/or the non-delivery period of the on/off cycle of the one or more aerosolized medicaments.

For example, referring to FIGS. 1 and 6, treatment calculation module 48 is configured to calculate, for each medicament and for each week, the number of daily treatments based on the number of chamber fills per treatment (information in column 604) and the clinician prescription (information in column 605). For each medicament, this is done by multiplying the data of columns 604 and 605. In order to perform the calculation for each medicament, treatment calculation module 48 determines if the particular medicament should be cycled on/off and, if so, if the medicament is in the delivery period or the non-delivery period. If the particular medicament should be cycled on/off and is in the delivery period, treatment calculation module 48 outputs the result of the multiplication in column 606. By contrast, if the particular medicament is in the non-delivery period, a zero is automatically outputted in column 606 by the treatment calculation module 48.

As mentioned previously, calculations are performed for each week of therapy. In one implementation, in advance of a given week of therapy, treatment calculation module 48 determines the number of daily treatments and/or the daily treatment time based on the prescription information shown in table 600 and provided by the user in the prescription data form (see also prescription view 500). Treatment calculation module 48 calculates the number of daily treatments and/or the daily treatment time for the prescribed medicaments without taking into account the medicament(s) that is/are in a non-delivery period for that particular week. Therefore, because calculations are performed for each week, treatment calculation module 48 is adapted to automatically change the total number of daily treatments and/or the daily treatment time for the prescribed medicament(s) when the therapy enters, or is about to enter, the delivery period and/or the non-delivery period of the on/off cycle of one or more aerosolized medicaments.

It will be appreciated that enabling automated change of the total number of daily treatments and/or the daily treatment time for the prescribed medicament(s) to be delivered to the subject provides various enhancements over previous systems. For example, this does not require an operator to change the prescription each time the therapy enters a non-delivery period or a delivery period so that the target lines 305, 306 and 307 in treatment view 300 are correct.

In one embodiment, during the non-delivery period of a particular medicament, the information/data related to that particular medicament are displayed in a different color, for example in grey, in prescription view 500. For example, FIG. 7 shows table 600 according to one embodiment. Table 600 includes two medicaments (Promixin and Tobramycin) that are delivered to the subject following an on/off cycle of a same duration. As shown in FIG. 7, Promixin is in the non-delivery period of its on/off cycle and has been schematically grayed out. This change of color will appear in prescription view 500. Tobramycin is delivered to the subject during the non-delivery period of Promixin. Once the delivery of Promixin enters its active delivery period, user interface module 44 will automatically generate a definition of a user interface in which Tobramycin will be grayed out and Promixin will not.

After obtaining the number of daily treatments for each medicament for a given week, treatment calculation module 48 is adapted to calculate the total number of treatments or nebulisations, TNT, to be delivered to the subject during that week. This is done by summing the number of daily treatments in columns 606. The output of the calculation, TNT, is shown in a box 608 of table 600 and displayed in line 305 of treatment view 300 and in prescription view 500. This target, represented by line 305, is important to show the subject if he/she is achieving the prescribed number of treatments.

Treatment calculation module 48 is further configured to calculate, for each medicament and for each week, the daily horn on time required to aerosolize the volume of medicament in the chamber of drug delivery device 12. The daily horn on time corresponds to the actuation time of the drug delivery device 12. In table 600 of FIG. 6, the daily horn on time is determined at a global delivery rate of 0.5 ml/min and is obtained using the chamber volume displayed in column 603 and the clinician prescription displayed in column 605. However, this is not limiting. It will be appreciated that the daily horn on time may be calculated at different delivery rates in other embodiments of the invention. Furthermore, in one embodiment, treatment calculation module 48 can use individual output rates for each medicament, as individual viscosities may vary, which may affect the output rate for that medicament and hence the daily horn on time.

In one embodiment, the daily horn of time for a particular week can be summed and divided by the total number of nebulizations, TNT, using the treatment calculation module 48 to give a mean daily horn on time for that week, which is displayed in a box 609 of table 600. This averaging is desirable to provide a target for the patient treatment time when using different medicaments. In order to provide the target treatment time for a particular week, indicated in line 306 in treatment view 300, treatment calculation module 48 multiplies the mean horn on time of box 609 by the nebulization factor TBM, as shown in equation 1 (eq. 1):

$$\text{treatment time}=\text{nebulization factor TBM}*(\text{mean horn on time}) \quad \text{(eq. 1)}$$

The actual treatment time can vary based on the patients inhalation manoeuvre, the mesh condition, medicament type, ambient conditions and the lung functions of the subject. In one embodiment, the nebulization factor TBM can be obtained for a particular medicament and for a particular drug delivery device and then used as a global variable to convert all medicament mean horn on times to a treatment target time for that particular drug delivery device. For example, the treatment time for Promixin using a 0.3 ml metering chamber of the 1-neb AAD manufactured by Philips is a mean of 4.3 min (Reference: Use of 1-neb AAD System Patient Logging System Data to Identify Aerosol Treatment Issues in Patients with CF, ATS 2007). Substituting these values into equation 1 gives a nebulization factor TBM of about 8. The nebulization factor TBM of 8 is then used by treatment calculation module 48 to convert all medicament mean horn times to a treatment time target, shown in line 306 of treatment view 300.

In one embodiment, the alert module 50 is configured to generate a signal that enables user interface module 48 to display a future period (for example, two weeks) on treatment view 300 to indicate that the user treatment is about to change as a result of the therapy entering a delivery period and/or a non-delivery period of one or more medicaments. For example, referring to FIG. 8, first graph 301 displays the expected or targeted total daily nebulizations for the first two weeks of therapy for February. As shown in FIG. 8, the expected or targeted total daily nebulizations will be reduced in February from 6 to 3, indicating that the therapy is about to enter a non-delivery period of a medicament (Tobramycin in FIG. 8). The advance notice for the change can be displayed one or several days in advance or one or several weeks in advance in user interface module 48.

The alerts generated by alert module 50 may be provided to the user and/or subject via the user interface defined by user interface module 48 and communicated to the subject via communications module 46. In one embodiment, the alerts generated by alert module 50 are delivered to subjects by communications module 46 via communications media other than the user interface defined by user interface module 48. For example, communications module 46 may transmit the alerts to the subjects via one or more of SMS and/or text message, email, other electronic text-based communication, voicemail, automated telephone call, and/or other communications media.

In addition, or alternatively, additional text can be added in graph 301 in a pop up box or a banner 309 to indicate or prompt that a treatment change is required, or to give additional information about the change. In one embodiment, additional information includes making additional clinical measurements to monitor the status of the therapy such as: taking a sputum sample, performing lung function measurements, and/or completing a questionnaire. In one embodiment, as shown in FIG. 9, these messages can be further highlighted in a box 310 by using color associated with the medicament type. This may be helpful if the change in therapy does not coincide with a change in the total nebulizations per day and hence the targeted or expected total daily nebulizations shown by line 305 on graph 301 has no step to define the change.

It will be appreciated that enabling automated notice to the user and/or the subject of a change of total number of daily treatments and/or daily treatment time for the prescribed medicament(s) provides various enhancements over previous systems. For example, this does not require an operator to inform the user and/or subject each time a medicament enters a non-delivery period or a delivery period, which is inefficient.

FIG. 10 illustrates a method 1000 of monitoring and/or managing the therapy of a plurality of subjects, wherein the therapy includes the delivery of aerosolized medicament with drug delivery devices. The operations of method 1000 presented below are intended to be illustrative. In some embodiments, method 1000 may be accomplished with one or more additional operations not described, and/or without one or more of the operations discussed. Additionally, the order in which the operations of method 1000 are illustrated in FIG. 10 and described below is not intended to be limiting.

In some embodiments, method 1000 may be implemented by a server including one or more processors (e.g., a digital processor, an analog processor, a digital circuit designed to process information, an analog circuit designed to process information, a state machine, and/or other mechanisms for electronically processing information) configured to execute one or more computer program modules. The one or more processors may include one or more devices executing some or all of the operations of method 1000 in response to instructions stored electronically on an electronic storage medium. The one or more processors may include one or more devices configured through hardware, firmware, and/or software to be specifically designed for execution of one or more of the operations of method 1000.

At an operation 1001, prescription information related to one or more aerosolized medicaments is obtained for a subject. In one embodiment, prescription information includes the number of daily treatments prescribed by the clinician, the chamber volume of a drug delivery device used in the delivery of the plurality of aerosolized medicaments, the number of chamber fills per treatment for each aerosolized medicament. In one embodiment, operation 1001 is performed by a information acquisition module that is the same as or similar to information acquisition module 38 (shown in FIG. 1 and described above).

At an operation 1002, it is determined if any of the aerosolized medicaments follows an on/off cycle. In one embodiment, the predetermined duration of the on/off cycle is also determined. In one embodiment, operation 1002 is performed by a treatment calculation module that is the same as or similar to treatment calculation module 48 (shown in FIG. 1 and described above).

At an operation 1003, a number of daily treatments for the one or more aerosolized medicaments to be delivered to the subject are calculated. Furthermore, a change in the number of daily treatments to be delivered to the subject is automatically calculated when the therapy enters the delivery period and/or the non-delivery period of the on/off cycle. In one embodiment, operation 1002 is performed by a treatment calculation module that is the same as or similar to treatment calculation module 48 (shown in FIG. 1 and described above).

At an operation 1004, one or more alerts are generated to a user and/or subject of the change in number of daily treatments performed at operation 1003. In one embodiment, operation 1004 is performed by alert module that is the same as or similar to alert module 50 (shown in FIG. 1 and described above).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A system configured to remotely monitor the therapy of at least one subject, wherein the therapy includes the delivery of a plurality of aerosolized medicaments with at least one drug delivery device and wherein at least one of the plurality of aerosolized medicaments is delivered following an on/off cycle of a predetermined duration of said at least one drug delivery device, said on/off cycle including a delivery period during which said at least one aerosolized medicament is delivered to said subject and a non-delivery period during which said at least one aerosolized medicament is not delivered to said subject, the system comprising:

the at least one drug delivery device; and a server in communication with the at least one drug delivery device comprising one or more processors configured to execute computer program modules, the computer program modules comprising:

(a) an information acquisition module configured to obtain, over a communications network, therapy information for said subject, wherein therapy information for said subject includes information related to a respiratory capacity of said subject and information conveying one or more breathing parameters of the respiration of said subject during the delivery of the plurality of aerosolized medicaments;

(b) a user interface module configured to generate a definition of a user interface that enables a user to selectively view said therapy information and to enter prescription data relating to said plurality of medicaments, wherein the user interface module is configured to define a treatment view of the user interface, the treatment view comprising information about a frequency and duration of treatments received by said subject during a previous period of time;

(c) a treatment calculation module configured to calculate (i) a total number of daily treatments to be delivered to said subject, with said at least one drug delivery device, based on said prescription data for individual ones of said plurality of aerosolized medicaments, wherein said calculation module is configured to automatically determine a change of the total number of daily treatments for the individual ones of said plurality of aerosolized medicaments when the therapy enters the delivery period and/or the non-delivery period of the on/off cycle of said at least one drug delivery device, (ii) a daily actuation time required to aerosolize the individual ones of said plurality of aerosolized medicaments in the at least one drug delivery device, and (iii) a treatment time target based on the daily actuation time and a nebulization factor corresponding to the individual ones of said plurality of aerosolized medicaments and the at least one drug delivery device, and cause the treatment view to display the treatment time target; and (d) an alert module configured to cause the treatment view to display information that indicates the change of the total number of daily treatments for the individual ones of said plurality of aerosolized medicaments for a future period of time when the therapy enters the delivery period and/or the non-delivery period of the on/off cycle with the information about the frequency and duration of treatments received by said subject during the previous period of time, wherein the display of information comprises one or more fields in the treatment view, the one or more fields displaying the total number of daily treatments for the individual ones of said plurality of aerosolized medicaments for the future period of time and the previous period of time, and displaying the change of the total number of daily treatments for the individual ones of said plurality of aerosolized medicaments for the future period of time, simultaneously with the total number of daily treatments for the individual ones of said plurality of aerosolized medicaments for the future period of time and the previous period of time.

2. The system of claim 1, wherein the alert module is configured to inform the user and/or said subject that the therapy is about to enter the delivery period and/or the non-delivery period of the on/off cycle.

3. The system of claim 2, wherein the alert module is configured to provide information related to a change of number of total daily nebulizations for the delivery of the plurality of aerosolized medicaments and/or a date at which the delivery period begins or ends.

4. The system of claim 1, wherein the prescription data includes the number of daily treatments prescribed by the clinician, the chamber volume of a drug delivery device used in the delivery of the plurality of aerosolized medicaments, the number of chamber fills per treatment for each aerosolized medicament, whether the aerosolized medicament should follow an on/off cycle, and/or the predetermined duration of the on/off cycle.

5. The system of claim 1, wherein the user interface module is further configured to define:

a device view of the user interface, the device view comprising information related to metrics that quantify drug delivery device performance of said at least one drug delivery device, the metrics comprising:

one or more of a mesh performance, a tidal breathing mode inhalation time, or a rest time; and a corresponding one or more of a targeted mesh performance, a targeted tidal breathing mode inhalation time, or a targeted rest time;

a prescription view of the user interface, the prescription view comprising information related to a therapy regime prescribed for a group of subjects including said subject;

a record view of the user interface, the record view comprising information related to historical device usage and respiratory function of the group of subjects including said subject; and a subject grouping view of the user interface, the subject grouping view configured to facilitate viewing, creation of, and/or manipulation of groupings of subjects including said subject.

6. The system of claim 1, wherein the alert module is configured to cause the treatment view to display the information that indicates the change of the total number of daily treatments for the individual ones of said plurality of aerosolized medicaments for a future period of time when the therapy enters the delivery period and/or the non-delivery period of the on/off cycle with the information about the frequency and duration of treatments received by said subject during the previous period of time via a graph visually displayed in the treatment view.

7. The system of claim 1, wherein the total number of daily treatments for the individual ones of said plurality of aerosolized medicaments for the future period of time and the previous period of time is displayed in a first field, and the change of the total number of daily treatments for the future period of time is displayed in a second field, separated by a boundary from the first field.

8. The system of claim 7, wherein the second field further includes additional information comprising information related to taking a sputum sample, lung function measurements, and/or completing a questionnaire.

9. The system of claim 1, wherein the treatment time target is calculated based on an average of the daily actuation time of the individual ones of said plurality of aerosolized medicaments and the nebulization factor.

10. A computer implemented method of remotely monitoring the therapy of at least one subject, wherein the therapy includes the delivery of a plurality of aerosolized medicaments with at least one drug delivery device and wherein at least one of the plurality of aerosolized medicaments is delivered following an on/off cycle of a predetermined duration of said at least one drug delivery device, said on/off cycle including a delivery period during which said at least one aerosolized medicament is delivered to said subject and a non-delivery period during which said at least one aerosolized medicament is not delivered to said subject, and wherein the method is implemented by a server comprising one or more processors configured to execute one or more computer program modules, the method comprising:

executing one or more computer program modules on the one or more processors of the server to obtain, over a communications network, therapy information for said subject, wherein therapy information for said subject includes information related to a respiratory capacity of the subject and information conveying one or more breathing parameters of the respiration of said subject during the delivery of the plurality of aerosolized medicaments;

executing one or more computer program modules on the one or more processors of the server to generate a definition of a user interface that enables a user to selectively view said therapy information and to enter prescription data relating to said plurality of medicaments, wherein the user interface comprises a treatment view, the treatment view comprising information about a frequency and duration of treatments received by said subject during a previous period of time;

executing one or more computer program modules on the one or more processors of the server to calculate (i) a total number of daily treatments to be delivered to said subject, with said at least one drug delivery device, based on said prescription data for individual ones of said plurality of aerosolized medicaments, wherein a change of said total number of daily treatments is automatically determined for the individual ones of said plurality of aerosolized medicaments when the therapy enters the delivery period and/or the non-delivery period of the on/off cycle of said at least one drug delivery device, (ii) a daily actuation time required to aerosolize the individual ones of said plurality of aerosolized medicaments in the at least one drug delivery device, and (iii) a treatment time target based on the daily actuation time and a nebulization factor corresponding to the individual ones of said plurality of aerosolized medicaments and the at least one drug delivery device, and cause the treatment view to display the treatment time target; and executing one or more computer program modules on the one or more processors of the server to cause the treatment view to display information that indicates the change of the total number of daily treatments for the individual ones of said plurality of aerosolized medicaments for a future period of time when the therapy enters the delivery period and/or the non-delivery period of the on/off cycle with the information about the frequency and duration of treatments received by said subject during the previous period of time, wherein the display of information comprises one or more fields in the treatment view, the one or more fields displaying the total number of daily treatments for the individual ones of said plurality of aerosolized medicaments for the future period of time and the previous period of time, and displaying the change of the total number of daily treatments for the individual ones of said plurality of aerosolized medicaments for the future period of time, simultaneously with the total number of daily treatments for the individual ones of said plurality of aerosolized medicaments for the future period of time and the previous period of time.

11. The method of claim 10, comprising executing one or more computer program modules on the one or more processors of the server to inform the user and/or said subject that said therapy is about to enter the delivery period and/or the non-delivery period of the on/off cycle.

12. The method of claim 11, wherein the information provided to the user include information related to a change of number of total daily nebulizations for the delivery of the plurality of aerosolized medicaments and/or a date at which the delivery period begins or ends.

13. The method of claim 10, wherein the prescription data includes the number of daily treatments prescribed by the clinician, the chamber volume of a drug delivery device used in the delivery of the plurality of aerosolized medicaments, the number of chamber fills per treatment for each aerosolized medicament, whether the aerosolized medicament should follow an on/off cycle, and/or the predetermined duration of the on/off cycle.

14. The method of claim 10, wherein the user interface comprises:

a device view of the user interface, the device view comprising information related to metrics that quantify drug delivery device performance of said at least one drug delivery device, the metrics comprising:

one or more of a mesh performance, a tidal breathing mode inhalation time, or a rest time; and a corresponding one or more of a targeted mesh performance, a targeted tidal breathing mode inhalation time, or a targeted rest time;

a prescription view of the user interface, the prescription view comprising information related to a therapy regime prescribed for a group of subjects including said subject;

a record view of the user interface, the record view comprising information related to historical device usage and respiratory function of the group of subjects including said subject; and a subject grouping view of the user interface, the subject grouping view configured to facilitate viewing, creation of, and/or manipulation of groupings of subjects including said subject.

15. The method of claim 10, further comprising causing the treatment view to display the information that indicates the change of the total number of daily treatments for the individual ones of said plurality of aerosolized medicaments for a future period of time when the therapy enters the delivery period and/or the non-delivery period of the on/off cycle with the information about the frequency and duration of treatments received by said subject during the previous period of time via a graph visually displayed in the treatment view.

16. The method of claim 10, wherein the displaying of the total number of daily treatments for the individual ones of said plurality of aerosolized medicaments for the future period of time and the previous period of time is in a first field, and the displaying of the change of the total number of daily treatments for the future period of time is in a second field, separated by a boundary from the first field.

17. The method of claim 16, wherein the second field further includes additional information comprising information related to taking a sputum sample, lung function measurements, and/or completing a questionnaire.

18. A system configured to remotely monitor the therapy of at least one subject, wherein the therapy includes the delivery of a plurality of aerosolized medicaments with said at least one drug delivery device and wherein at least one of the plurality of aerosolized medicaments is delivered following an on/off cycle of a predetermined duration of said at least one drug delivery device, said on/off cycle including a delivery period during which said at least one aerosolized medicament is delivered to said subject and a non-delivery period during which said at least one aerosolized medicament is not delivered to said subject, the system comprising:

the at least one drug delivery device; and means for obtaining, over a communications network, therapy information for said subject, wherein therapy information for said subject includes information related to a respiratory capacity of said subject and information conveying one or more breathing parameters of the respiration of said subject during the delivery of the plurality of aerosolized medicaments;

means for generating a definition of a user interface that enables a user to selectively view said therapy information and to enter prescription data relating to said plurality of medicaments, wherein the user interface comprises a treatment view, the treatment view comprising information about a frequency and duration of treatments received by said subject during a previous period of time;

means for calculating:

(i) a total number of daily treatments to be delivered to said subject, with said at least one drug delivery device, based on said prescription data for individual ones of said plurality of aerosolized medicaments, wherein a change of said total number of daily treatments is automatically determined for the individual ones of said plurality of aerosolized medicaments when the therapy enters the delivery period and/or the non-delivery period of the on/off cycle of said at least one drug delivery device, (ii) a daily actuation time required to aerosolize the individual ones of said plurality of aerosolized medicaments in the at least one drug delivery device, and (iii) a treatment time target based on the daily actuation time and a nebulization factor corresponding to the individual ones of said plurality of aerosolized medicaments and the at least one drug delivery device, and cause the treatment view to display the treatment time target; and means for causing the treatment view to display information that indicates the change of the total number of daily treatments for the individual ones of said plurality of aerosolized medicaments for a future period of time when the therapy enters the delivery period and/or the non-delivery period of the on/off cycle with the information about the frequency and duration of treatments received by said subject during the previous period of time, wherein the display of information comprises one or more fields in the treatment view, the one or more fields displaying the total number of daily treatments for the individual ones of said plurality of aerosolized medicaments for the future period of time and the previous period of time, and displaying the change of the total number of daily treatments for the individual ones of said plurality of aerosolized medicaments for the future period of time, simultaneously with the total number of daily treatments for the individual ones of said plurality of aerosolized medicaments for the future period of time and the previous period of time.

19. The system of claim 18, comprising means for informing the user and/or said subject that said at least one aerosolized medicament is about to enter the delivery period and/or the non-delivery period of the on/off cycle.

20. The system of claim 19, wherein the information provided to the user include information related to a change of number of total daily nebulizations for the delivery of the plurality of aerosolized medicaments and/or a date at which the delivery period begins or ends.

21. The system of claim 18, wherein the prescription data includes the number of daily treatment prescribed by the clinician, the chamber volume of a drug delivery device used in the delivery of the plurality of aerosolized medicaments, the number of chamber fills per treatment for each aerosolized medicament, whether the aerosolized medicament should follow an on/off cycle, and/or the predetermined duration of the on/off cycle.

22. The system of claim 18, wherein the user interface comprises:

a device view of the user interface, the device view comprising information related to metrics that quantify drug delivery device performance of said at least one drug delivery device, the metrics comprising:

one or more of a mesh performance, a tidal breathing mode inhalation time, or a rest time; and a corresponding one or more of a targeted mesh performance, a targeted tidal breathing mode inhalation time, or a targeted rest time;

a prescription view of the user interface, the prescription view comprising information related to a therapy regime prescribed for a group of subjects including said subject;

a record view of the user interface, the record view comprising information related to historical device usage and respiratory function of the group of subjects including said subject; and a subject grouping view of the user interface, the subject grouping view configured to facilitate viewing, creation of, and/or manipulation of groupings of subjects including said subject.

23. The system of claim 18, further comprising means for causing the treatment view to display the information that indicates the change of the total number of daily treatments for the individual ones of said plurality of aerosolized medicaments for a future period of time when the therapy enters the delivery period and/or the non-delivery period of the on/off cycle with the information about the frequency and duration of treatments received by said subject during the previous period of time via a graph visually displayed in the treatment view.

24. The system of claim 18, wherein the total number of daily treatments for the individual ones of said plurality of aerosolized medicaments for the future period of time and the previous period of time is displayed in a first field, and the change of the total number of daily treatments for the future period of time is displayed in a second field, separated by a boundary from the first field.

25. The system of claim 24, wherein the second field further includes additional information comprising information related to taking a sputum sample, lung function measurements, and/or completing a questionnaire.

* * * * *